(12) United States Patent  
Sen et al.

(10) Patent No.: US 11,883,119 B2
(45) Date of Patent: *Jan. 30, 2024

(54) CORRECTING A ROBOTIC SURGERY USER INTERFACE DEVICE TRACKING INPUT

(71) Applicant: Verb Surgical Inc., Santa Clara, CA (US)

(72) Inventors: Hasan Tutkun Sen, San Mateo, CA (US); Sina Nia Kosari, Fremont, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/878,670

(22) Filed: Aug. 1, 2022

(65) Prior Publication Data

US 2022/0378532 A1 Dec. 1, 2022

Related U.S. Application Data

(60) Continuation of application No. 17/110,928, filed on Dec. 3, 2020, now Pat. No. 11,413,101, which is a
(Continued)

(51) Int. Cl.
*A61B 34/32* (2016.01)
*G06F 3/0346* (2013.01)
(Continued)

(52) U.S. Cl.
CPC .............. *A61B 34/32* (2016.02); *A61B 34/30* (2016.02); *A61B 34/74* (2016.02); *B25J 3/00* (2013.01);
(Continued)

(58) Field of Classification Search
CPC ......... A61B 34/32; A61B 34/30; A61B 34/74; A61B 2034/104; A61B 2034/2048;
(Continued)

(56) References Cited

U.S. PATENT DOCUMENTS

| 4,442,404 | A | 4/1984 | Bergmann |
| 7,453,227 | B2* | 11/2008 | Prisco ................... B25J 9/1689 700/254 |

(Continued)

FOREIGN PATENT DOCUMENTS

| WO | 2006091494 | 8/2006 |
| WO | 2007136768 | 11/2007 |

OTHER PUBLICATIONS

International Preliminary Report on Patentability for International Application No. PCT/US2018/019774 dated Sep. 3, 2020, 6 pages.
(Continued)

*Primary Examiner* — Tung S Lau
(74) *Attorney, Agent, or Firm* — Aikin & Gallant, LLP

(57) ABSTRACT

A sequence of input samples that are measures of position or orientation of an input device being held by a user are received. A current output sample of a state of linear quadratic estimator, LQE, is computed that is an estimate of the position or orientation of the input device. The current output sample is computed based on i) a previously computed output sample, and ii) a velocity term. An updated output sample of the state of the LQE is computed, based on i) a previously computed output sample, and ii) a new input sample. Other embodiments are also described and claimed.

20 Claims, 4 Drawing Sheets

Related U.S. Application Data division of application No. 15/900,552, filed on Feb. 20, 2018, now Pat. No. 10,881,472.

(51) Int. Cl.

| | |
|---|---|
| *G06F 3/038* | (2013.01) |
| *A61B 34/00* | (2016.01) |
| *B25J 3/00* | (2006.01) |
| *B25J 13/08* | (2006.01) |
| *B25J 15/00* | (2006.01) |
| *B25J 9/16* | (2006.01) |
| *A61B 34/30* | (2016.01) |

(52) U.S. Cl.
CPC ............. *B25J 9/161* (2013.01); *B25J 13/088* (2013.01); *B25J 15/0019* (2013.01); *G06F 3/038* (2013.01); *G06F 3/0346* (2013.01); *Y10S 901/02* (2013.01); *Y10S 901/41* (2013.01); *Y10S 901/46* (2013.01)

(58) Field of Classification Search
CPC .... A61B 2034/2055; A61B 2034/2051; A61B 34/20; B25J 30/00; B25J 9/161; B25J 13/088; B25J 15/0019; B25J 9/1664; B25J 9/163; B25J 9/1653; B25J 9/1689; G06F 3/0346; G06F 3/038; Y10S 901/02; Y10S 901/41; Y10S 901/46; G05B 2219/40195

See application file for complete search history.

(56) References Cited

U.S. PATENT DOCUMENTS

| | | | | |
|---|---|---|---|---|
| 8,073,528 | B2* | 12/2011 | Zhao | G16H 40/67 700/245 |
| 8,079,950 | B2* | 12/2011 | Stern | A61B 34/70 600/109 |
| 8,287,522 | B2 | 10/2012 | Moses et al. | |
| 8,613,724 | B2 | 12/2013 | Lanier, Jr. et al. | |
| 8,996,169 | B2* | 3/2015 | Lightcap | B25J 9/1689 700/250 |
| 9,220,917 | B2 | 12/2015 | Boyden et al. | |
| 9,296,104 | B2 | 3/2016 | Swarup et al. | |
| 9,727,963 | B2* | 8/2017 | Mintz | G06T 7/149 |
| 9,861,447 | B2* | 1/2018 | Hourtash | B25J 9/16 |
| 11,071,441 | B2* | 7/2021 | Yu | H02P 5/56 |
| 11,076,918 | B2* | 8/2021 | Quaid, III | B25J 13/025 |
| 11,413,101 | B2* | 8/2022 | Sen | A61B 34/30 |
| 2006/0142657 | A1 | 6/2006 | Quaid et al. | |
| 2006/0258938 | A1 | 11/2006 | Hoffman et al. | |
| 2007/0252550 | A1 | 11/2007 | Takaishi | |
| 2012/0041263 | A1* | 2/2012 | Sholev | A61B 90/98 600/118 |
| 2013/0064427 | A1* | 3/2013 | Picard | G01S 5/163 382/103 |
| 2013/0218340 | A1* | 8/2013 | Hager | B25J 9/1671 700/257 |
| 2014/0249654 | A1 | 9/2014 | Blevins et al. | |
| 2015/0018841 | A1 | 1/2015 | Seo | |
| 2015/0164609 | A1* | 6/2015 | Wu | A61B 34/30 600/424 |
| 2016/0025756 | A1 | 1/2016 | Pollack et al. | |
| 2017/0036346 | A1 | 2/2017 | Kamioka | |
| 2017/0084027 | A1* | 3/2017 | Mintz | A61B 1/0016 |
| 2017/0252111 | A1* | 9/2017 | Wu | A61B 90/39 |
| 2018/0232048 | A1 | 8/2018 | Popovich et al. | |
| 2019/0041634 | A1 | 2/2019 | Popovich et al. | |
| 2019/0095644 | A1 | 3/2019 | Park et al. | |
| 2019/0380794 | A1 | 12/2019 | Al Jewad et al. | |

OTHER PUBLICATIONS

Wang, Yuguan, et al., "Filling the Gap between Low Frequency Measurements with Their Estimates," Robotics and Automation (ICRA), 2014 IEEE International Conference on, May 31, 2014, 6 pages.

Eom, Ki Hwan, "Improved Kalman Filter Method for Measurement Noise Reduction in Multi Sensor RFID Systems," Sensors, vol. 11, Oct. 28, 2011, pp. 10266-10282.

Tully, Stephen, et al., "Inequality Constrained Kalman Filtering for the Localization and Registration of a Surgical Robot," Intelligent Robots and Systems (IROS), 2011 IEEE/RSJ International Conference on, Sep. 1, 2011, 7 pages.

Negenborn, Rudy, "Robot Localization and Kalman Filters: On Finding your position in a noisy world," A thesis submitted to the Institute of Information and Computing Sciences in partial fulfillment of the requirements for the degree of Master of Science, specialized in Intelligent Systems, Sep. 1, 2003, 156 pages.

Kalman, R.E., "A New Approach to Linear Filtering and Predication Problems," Transactions of the ASME—Journal of Basic Engineering, 82(Series D), Jan. 1, 1960, 12 pages.

International Search Report and Written Opinion for International Application No. PCT/US2018/019774 dated Nov. 13, 2018, 10 pages.

Ramadurai, Srikrishnan, et al., "Application of Unscented Kalman Filter to a Cable Driven Surgical Robot: A Simulation Study," 2012 IEEE International Conference on Robotics and Automation, May 14, 2012, pp. 1495-1500.

Aravind, M.A., et al. "Optimal Position Control of a DC Motor Using LQG with EKF," 2017 International Conference on Mechanical, System and Control Engineering, 2017, pp. 149-154.

Gudpati, Mounika S.K., "Application of Kalman Filter to Estimate Position of a Mobile Node in Indoor Environments," May 2017, 55 pages.

Shala, Ubejd, et al., "Indoor Positioning using Sensor-fusion in Android Devices," Sep. 2011, 58 pages.

Extended European Search Report for European Application No. 18907327.3 dated Sep. 29, 2021, 11 pages.

* cited by examiner

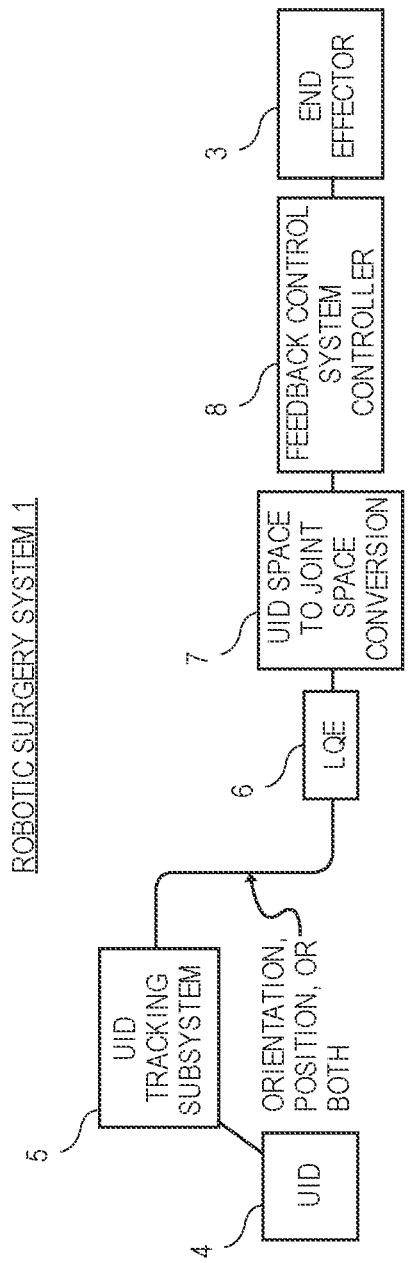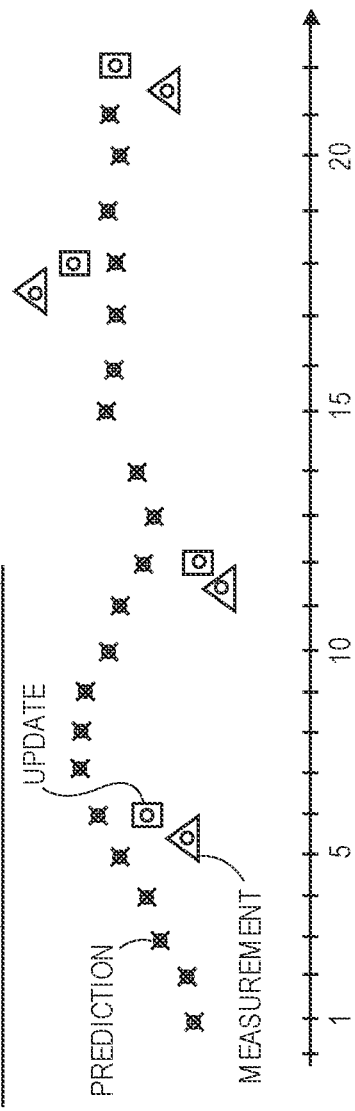

CORRECTING A ROBOTIC SURGERY USER INTERFACE DEVICE TRACKING INPUT

This patent application is continuation of U.S. Ser. No. 17/110,928 filed 3 Dec. 2020 which is a divisional of U.S. Ser. No. 15/900,552 filed Feb. 20, 2018.

FIELD

An embodiment of the invention relates to digital signal processing techniques for correcting a sensor circuit-generated signal that tracks the orientation or position of a handheld, robotic surgery user interface device. Other embodiments are also described.

BACKGROUND

In the field of robotic surgery, the movements of a user interface device (UID) such as a handheld manipulator (held in the surgeon's hand) are translated into corresponding movements of a joint on a robotic or manipulator arm to which a surgical tool is attached (also referred to as end effector.) This may give the surgeon greater visualization, enhanced dexterity, and greater precision, which benefit the patient in many ways including shorter hospitalization, faster recovery, and smaller incisions. A digital stream of sensed orientation data and position data, that may be time-stamped or that may be updated regularly according to a clock signal, is produced by a sensor subsystem. The stream represents real-time tracking of the UIDs orientation and position, also referred to as robotic surgery UID tracking (orientation and position) data. A part or all of the sensor subsystem may be inside the housing of the UID, e.g., using the raw output from inertial sensors such as an accelerometer and a gyro that are inside the UID housing. The UID tracking data may also be produced by a sensor subsystem such as a six-degree of freedom (6DOF) electromagnetic tracker that is suitable for medical or surgical applications, or by an optical tracker that is "looking" at markers on the UID. The tracking data may be relative (e.g., incremental displacement or orientation changes) or it may be absolute.

The tracking data is an input to a robotic surgery controller that translates the tracking data, which is a direct measure of the movement of the UID, into corresponding actuator commands for an end effector, so that the end effector mimics the movements of the UID (that are caused by for example the surgeon's hand, wrist and fingers.) As a practical matter, however, the tracking data (tracking input) is noisy or imprecise, and therefore needs to be corrected in order to ensure precision and repeatability in the movement of the end effector. In addition, while the tracking input may be time-stamped or it may be isochronous, its constituent measured values (measured samples) might have been produced or delivered by the sensor circuit at a different rate than desired by the robotic surgery controller that is consuming the tracking input, e.g., the sensor circuit sampling rate may be slower than the sample rate of a discrete time domain (digital) controller.

SUMMARY

An embodiment of the invention is a linear quadratic estimator, LQE, that corrects a noisy or imprecise robotic surgery UID tracking input, and may also inherently up-sample the tracking input to come closer to or match the higher input sample rate of a robotic surgery control system controller, and may do so without introducing an unduly high latency. In one embodiment, the LQE (or corrector) integrates the latency reduction and up-sampling functions into its prediction phase that is repeating at a higher rate than the UID tracking input to produce output samples, and switches to its update phase when a new tracking input sample is received. In the update phase, a Kalman filter gain may be computed that is used to compute an updated output sample of the LQE. In one embodiment, a latency coefficient used in the prediction phase has been tuned in advance, so that the LQE output exhibits reduced latency.

In another embodiment, a robotic surgery system has a processor and a machine-readable medium having stored therein instructions that when executed by the processor correct a UID tracking input, by producing an output sequence that is an estimate of a position or an orientation of the UID. The processor receives an input sequence that are measures of the position or the orientation of the UID, and computes a current output sample of the output sequence, wherein the current output sample is computed based on i) a previously computed output sample, and ii) a velocity term. When a new tracking input sample of the input sequence is received, a new output sample of the output sequence is computed, based on i) a previously computed output sample, and ii) the new tracking input sample. In one instance, the instructions are such that while the new tracking input sample has not been received, the current output sample in the output sequence is computed from a window of several previously computed output samples, by a) fitting a line to the previously computed output samples in the window, and b) taking a slope of the line to be the velocity term.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

FIG. 1 is a block diagram of an example robotic surgery system.

FIG. 3 is an example plot of LQE output samples overlaid with tracking input measurement samples.

DETAILED DESCRIPTION

Figure 2:
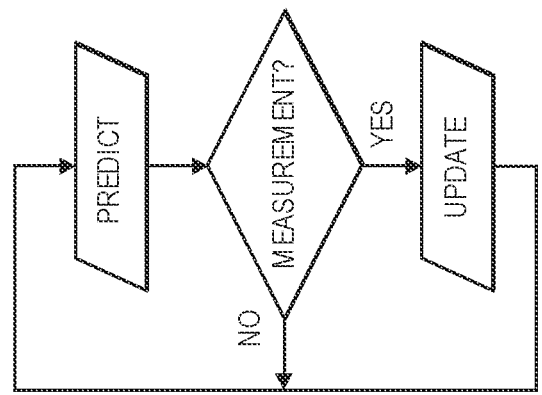
FIG. 2 is a flow diagram of a linear quadratic estimation process.

Several embodiments of the invention with reference to the appended drawings are now explained. Whenever the shapes, relative positions and other aspects of the parts described in the embodiments are not explicitly defined, the scope of the invention is not limited only to the parts shown, which are meant merely for the purpose of illustration. Also, while numerous details are set forth, it is understood that some embodiments of the invention may be practiced without these details. In other instances, well-known circuits, structures, and techniques have not been shown in detail so as not to obscure the understanding of this description.

A conventional linear quadratic estimator, LQE, has a prediction phase in which a system model is used to compute estimates of an output state variable (also referred to here as "output"), and an update phase in which the outcome of the present input measurement (which is of course corrupted by noise or imprecision) is used to update the estimates so that they tend to be more precise than the input measurements. The LQEs algorithm is recursive and can run in real time, using only the present input measurements and the previously calculated output (and its uncertainty matrix.)

An embodiment of the invention is a modified LQE or corrector that is particularly suitable for correcting the position, orientation or both of a robotic surgery UID, as represented in a tracking input sequence. The tracking input sequence may also be referred to here as a tracking input, or input measurement, and may be that of several position variables, several orientation variables, or both. FIG. 1 is a block diagram of an example robotic surgery system 1 in which the modified LQE, LQE 6, is used. In the robotic surgery system 1, the movements of a user interface device, UID 4, such as a handheld manipulator (held in the surgeon's hand) are translated into corresponding movements of a joint on a robotic or manipulator arm to which a surgical tool is attached, also referred to here as an end effector 3. This may give the surgeon greater visualization, enhanced dexterity, and greater precision, which benefit the patient in many ways including shorter hospitalization, faster recovery, and smaller incisions. A digital stream of sensed orientation data and position data, that may be time-stamped or that may be updated regularly according to a clock signal, is produced by a UID tracking subsystem 5. The stream represents real-time tracking of the orientation and position of the UID 4, also referred to as robotic surgery UID tracking data (orientation data, position data, or both.) A part or all of the UID tracking subsystem 5 may be inside the housing of the UID 4, e.g., using the raw output from inertial sensors such as an accelerometer and a gyro that are inside the UID housing. The UID tracking data may also be produced by a sensor subsystem such as a six-degree of freedom (6DOF) electromagnetic tracker that is suitable for medical or surgical applications, or by an optical tracker that is "looking" at markers on the UID 4. The tracking data may be relative (e.g., incremental displacement or orientation changes) or it may be absolute. The tracking data is an input to a feedback control system controller 8 that translates the tracking data, which is a direct measure of the movement of the UID 4, into corresponding actuator commands for an end effector 3, so that the end effector 3 mimics the movements of the UID 4 (that are caused by for example the surgeon's hand, wrist and fingers.) There may be a UID space to joint space conversion 7 of the tracking input, before the tracking data is consumed by the controller 8.

As a practical matter, the tracking input produced by the UID tracking subsystem 5 is noisy or imprecise, and therefore needs to be corrected in order to ensure precision and repeatability in the movement of the end effector 3. In addition, while the tracking input may be time-stamped or it may be isochronous, its constituent measured values (measured samples) may have been produced or delivered by the sensor circuit (in the subsystem 5) at a different rate than desired by the controller 8 that is consuming the tracking input, e.g., the sensor circuit sampling rate may be slower than the sample rate of a discrete time domain (digital) controller. A linear quadratic estimator, LQE 6, is thus provided to correct the tracking input.

In one embodiment, the LQE 6 may be described as having a prediction phase and an update phase, which together recursively compute the samples of an LQE state variable (output), such as position, in accordance with the flow diagram of FIG. 2. Note that a similar description applies to orientation state variables albeit with more complex mathematics as explained further below. The flow diagram of FIG. 2 may produce the example discrete time sequence shown in FIG. 3, where operation begins with a current (or next) sample of the output state variable of the LQE (e.g., an output vector containing position values, orientation values, or both) being computed in the prediction phase, as a "prediction" at sample 1. As described below, this is done using a system model of the UID 4 and using a previous (or earlier in time) sample of the output state variable. Staying with FIG. 3, the LQE 6 produces its output samples 2-5 by repeating its prediction phase four times, until a new tracking input sample Xmeas is received in between sample 5 and sample 6 ("measurement".) At that point, the algorithm switches to its update phase in which an updated output "update" is computed at sample 6. The process then resumes with the prediction phase which is repeated to produce samples 7-11 until another new tracking input sample arrives in between sample 11 and sample 12, the latter causing a switch to the update phase to compute another updated output at sample 12. The next output samples 13-17 are produced in the prediction phase, followed with another updated output sample 18.

Also note that prior to sample 1, there may be an initialization stage in which the initial output state value (sample 1) is computed based on an input state (the tracking input or a measurement) or other initial condition, following which the next output state variable (sample 2 and subsequent samples) are computed recursively based on a previously computed output state value.

Prediction Phase

The prediction phase of the LQE 6 may be illustrated using the following example of a constant velocity mathematical system model, for position variable X. At a given point in time, t, the position of a particle may be represented by a continuous time system model, $$X = X0 + V0*t + \frac{1}{2}*A*t^2 \qquad (1)$$

X0=Previous position, t=0
V0=previous velocity, t=0
A=0 (acceleration) is assumed In one embodiment, the state variable X is a vector, X=[x, y, z, q0, q1, q2, q3] of Cartesian coordinates (x, y, z) as position data, and the quaternion (q0, q1, q2, q3) as orientation data. Note however that the LQE 6 may alternatively be applied to correct just the orientation data, while a non-estimating type low pass filter, e.g., a digital finite impulse response, FIR, filter, is applied to reduce noise in the position data only.

When the LQE 6 is implemented using a digital computer, a discrete time system model can be written as $$X[n+1]=X[n]+V*\text{delta\_}t+\text{noise} \quad (2)$$

This equation may be used to compute the state variable X at time index n+1 (also referred to as a current output sample X[n+1]). That computation is based on i) a previously computed output sample X[n], ii) a computed velocity term V, and iii) an inter-sample time interval delta_t (that as described below has been adjusted by a tuning parameter, alpha.) Note that delta_t may refer to the time interval used in the system model to compute a current sample at index n+1 from a previous sample at index n, in the prediction phase (it is not the tracking input's sampling period, which is lower than the rate at which predictions are computed in the prediction phase.) It can be seen from Eq. 2 above that in addition to the previous estimate of the state X[n], the computation of X[n+1] relies on two primary terms, namely delta_t and a computation of the velocity term V both of which are described below in turn. Also, the velocity term V here is not a "state" of the LQE as is X, but rather an input or external term. As to the noise term, it may be assumed to be Gaussian noise with zero mean and a sigma standard deviation.

Update Phase

The update phase may use any conventional measurement model (that is applicable to the UID and its tracking data) to compute an updated output, Xupd (an "update" data point in FIG. 2.) The measurement model used may be $$X\text{meas}=X[n+1]+\text{noise} \quad (3)$$

where Xmeas is the position (x-y-z) measurement or tracking input and X[n+1] is the predicted state calculated in Eq. 2. The measurement noise term may be modeled by collecting UID position data (tracking input) at different positions and orientations of the UID 4 and then by calculating its histogram.

The update phase may proceed as follows: compare Xmeas with Xpred (e.g., a previously computed output, X[n+1]), and use a measure of that comparison to compute a Kalman gain, K, using a particular measurement model; if the difference between Xmeas and Xpred is large, then K becomes larger, and if the difference is small then K becomes smaller. The gain K is then used to compute the updated position Xupd, as $$X\text{upd}=X\text{pred}+K*(\ldots) \quad (4)$$

where known techniques can be used to compute the $K*(\ldots)$ term. Xupd may then be taken as the updated, current output sample of the LQE (in this example, X[n+1].) The modified LQE may then proceed with computing the next output sample, here X[n+2], using its prediction phase operations as described above, and until another new tracking input is received that triggers the update phase.

Up-Sampling

From the above description, it is clear that the up-sampling of the tracking input by the modified LQE happens inherently when repeating the prediction phase at a higher rate than the tracking input sampling. Computation of X as the output state repeats until a new (e.g., a most recent) tracking input sample Xmeas arrives—see FIG. 3. Thus, the up-sampling function may be viewed as being performed during the prediction phase, according to the decision loop depicted in FIG. 2: if there is no new tracking input sample, then predict the output state, and then repeat that prediction until there is a new tracking input sample at which point the output state is updated in accordance with the new tracking input sample (e.g., and in accordance with a new Kalman filter gain.)

Note that a further advantage of the above process is that the prediction and update phases may occur asynchronously, which allows up sampling to be performed as needed to fill in the "gap" between adjacent tracking input samples. For instance, in FIG. 3, it can be seen that the first three series of consecutive predicted outputs (preceding the first three measurements) are each five samples long, whereas the fourth series is only three samples long (because the fourth measurement arrived sooner in that instance.)

Prediction Phase-Latency Coefficient

One problem that arises is how to reduce latency of the LQE 6. In accordance with an embodiment of the invention, a tuning parameter, also referred to here as a latency coefficient, alpha, is defined such that a sum of alpha and a nominal output sampling period nominal_period for the LQE's output sequence, replaces delta_t in the discrete time system model equation above, as $$\text{delta\_}t=\text{nominal\_period}+\text{alpha} \quad (5)$$

Note that nominal_period is the nominal LQE output sampling period and is the same (constant) for a batch of UIDs and their respective tracking input correctors, while alpha is a tuning parameter that varies from specimen to specimen of that batch. For example, the nominal_period=1 msec, and alpha is a fraction of the nominal_period but may vary depending on the application (the particular UID and its sensor-generated tracking input.)

Figure 4:
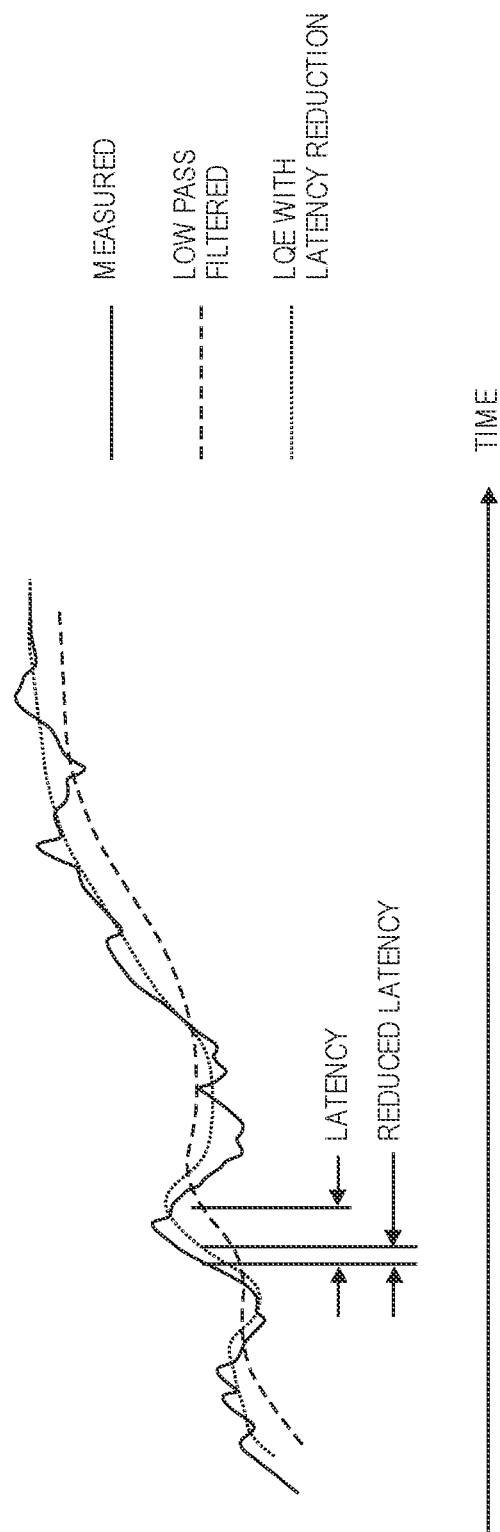
FIG. 4 depicts example plots of a tracking input (measured), overlaid with a low pass filtered version and an LQE processed version.

The latency coefficient alpha should be adjusted during a "calibration process", e.g., at the factory, for each production UID specimen, until the LQE output (which is being computed in accordance with the prediction and update phases as described further below) properly predicts "what is going to happen", by effectively shifting the LQE output sequence earlier in time, closer to the tracking input. This is illustrated in FIG. 4, where it can be seen that alpha has been varied until the output of the LQE 6 during a given trajectory of the particular specimen of the UID is shifted to the left, to lie "on top" of the measured signal (UID tracking input.) FIG. 4 shows this reduction in latency in contrast to the rather "delayed" behavior of a non-estimating low pass filter, acting on the same measured signal. After the value of alpha has been selected to achieve this desired result, the UID specimen may be shipped with this tuned alpha. The expectation is that the LQE output will now exhibit reduced latency during in-the-field use.

While the addition of (and the tuning of) alpha causes a reduction in the effective latency of the LQE 6 coupled with improved noise reduction in the output state, this comes at the cost of (or in exchange for) the LQE output exhibiting overshoot when the tracking input changes direction. There is a need to recover quickly from this overshoot; the LQE 6 performs this recovery in its update phase.

Prediction Phase-Computation of the Velocity Term

Another problem that arises in the LQE prediction phase is how to calculate V to avoid taking the derivative of the known but noisy tracking input, X_meas. Proper computation of V helps further reduce noise at the output of the LQE 6, and has been shown to influence the choice of the tuning parameter alpha. In one embodiment of the invention, referring now to FIG. 5, V may be computed from a window of previously computed output samples, $X[n-1]$, $X[n-2]$, ... $X[n-k]$ by fitting a line to the sequence of k output samples in the window, and then taking the slope of that line to be the velocity V. The fitted line may be defined by a continuous polynomial, which may be of first order so as to define a straight line as shown in the figure, or it may be of a higher order which defines a curved line. This parameterization of the position variable X with respect to time, to yield a continuous line and then determine the slope of the line, e.g., its derivative, is an advantageous feature because it inherently results in a smooth velocity estimate, V.

Figure 5:
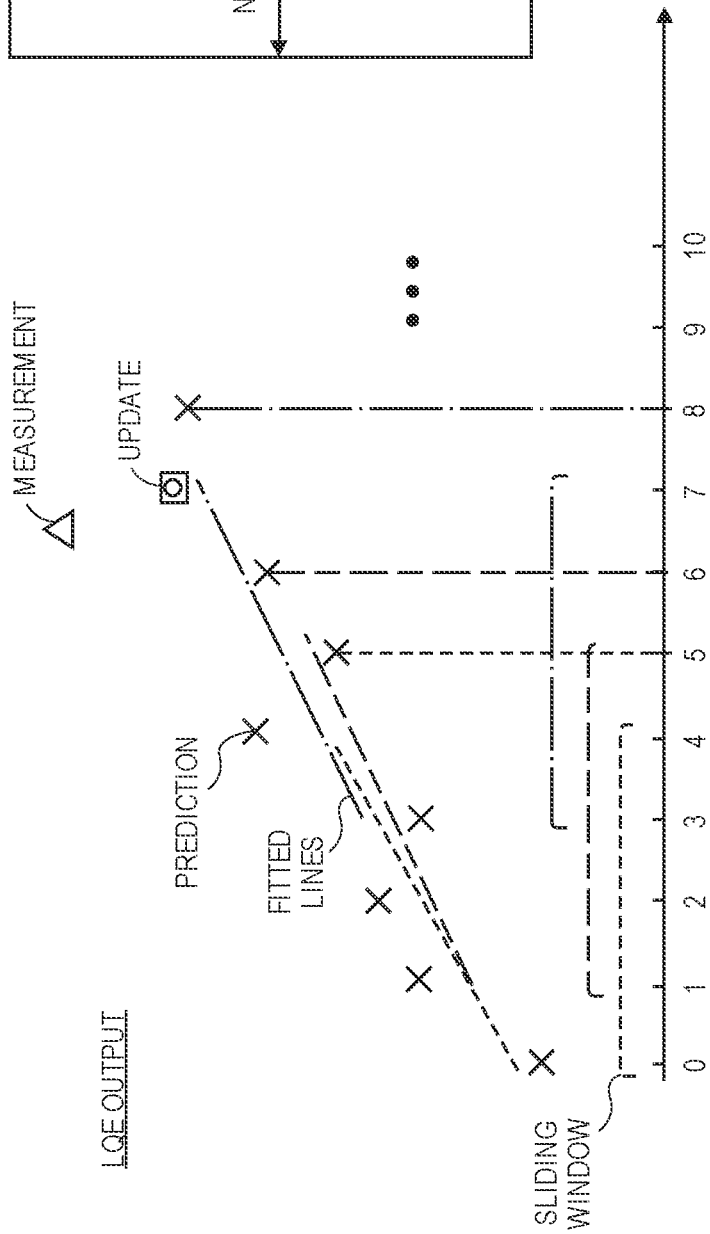
FIG. 5 is an example plot of prediction values that are computed using a sliding window and using fitted lines.

In the example shown in FIG. 5, a first order polynomial is fitted to the window of prior position estimates, with respect to time, as given by the polynomial equation $$X(t)=A*t+B \tag{6}$$

Note that the position data may include x, y and z values, such that A and B may be 3×1 vectors representing the polynomial coefficients for the three direction, x, y and z. The derivative of Eq. 5 is taken with respect to time to calculate the linear velocities V (in the x-y-z directions) as $$dX(t)/dt=V(t)=A \tag{7}$$

Note that the length k of the window (the number of samples in it) may be viewed as a second calibration parameter that can be used when tuning the latency coefficient alpha (see above.) Also, the window of length k moves or slides as shown in FIG. 5, each time the prediction phase is repeated to make a new prediction (e.g., the last k position values will change as shown), and so the computed velocity V changes for each prediction.

Also, the system model used in the prediction phase need not change and may remain the same for every prediction, while the window of state values that are used to parameterize the position state variable (and compute the velocity) does move in time and so changes with each new prediction.

Orientation Prediction Phase and Update Phase

The description above used position only, as the tracking input, to illustrate the various concepts in an easier to understand manner. The concepts described above however are also applicable to and in fact may be more relevant when applied to orientation data in the tracking input. In that case, the orientation states, quaternions (q0, q1, q2, q3) may be assumed to evolve with a constant angular velocity model as seen in the equation below:

$$q[n+1]=\exp(\tfrac{1}{2}*\mathrm{skew}(w*(\mathrm{nominal\_period+latency\_parameter})))*q[n]+\mathrm{noise} \tag{8}$$

where q is a 4×1 quaternion vector, w is a 3×1 angular velocity vector around x, y, or z axis, and is used as an input term not as a state variable, skew( ) is the skew symmetric matrix operation, nominal_period is the nominal LQE output sampling period as described above in connection with Eq. 5, and latency_parameter is a tuning parameter (like alpha above) to account for latency. The noise term may again be assumed to be Gaussian noise with zero mean and sigma standard deviation.

Similar to the position estimation case illustrated above, in order to have smooth angular velocity estimates, the quaternion estimates are parameterized with respect to time and their derivatives are taken. To do this one case use the slerp equation $$q(q0,q1,t)=q0*\sin[(1-t)\Omega]/\sin(\Omega)+q1*\sin[t\Omega]/\sin(\Omega) \tag{9}$$

where q0 and q1 are 4×1 quaternion vectors corresponding to the estimated quaternions, window_length outputs before and the last output, respectively, as given by $$q0=q[n-\mathrm{window\_length}]\,q1=q[n] \tag{10}$$

Additionally in Eq. 9, $\Omega$ corresponds to the angle between q1 and q2, and finally t is the time variable.

In order to obtain a continuous function of the angular velocity with respect to time, Eq. 9 is differentiated to obtain q_dot $$q\_\mathrm{dot}=dq/dt \tag{11}$$

Next Eq. 11 is used to find the angular orientation using $$w=2*\mathrm{transpose}(Q(q[n]))*q\_\mathrm{dot} \tag{12}$$

where Q is a 4×3 matrix formed by the latest quaternion estimate q[n] and it is calculated as $$Q = \begin{bmatrix} -q_2 & -q_3 & -q_4 \\ q_1 & -q_4 & q_3 \\ q_4 & q_1 & -q_2 \\ -q_3 & q_2 & q_1 \end{bmatrix} \tag{13}$$

In the update phase, the UID tracking input is used to update the quaternion orientation estimates. The measurement model used in the update phase may be $$q\_\mathrm{uid}=q[n+1]+\mathrm{noise} \tag{14}$$

where q_uid is the quaternion measurement (UID tracking input) and q[n+1] is the predicted state calculated in Eq. 8. The measurement noise term may be modeled similar to the position case.

Figure 6:
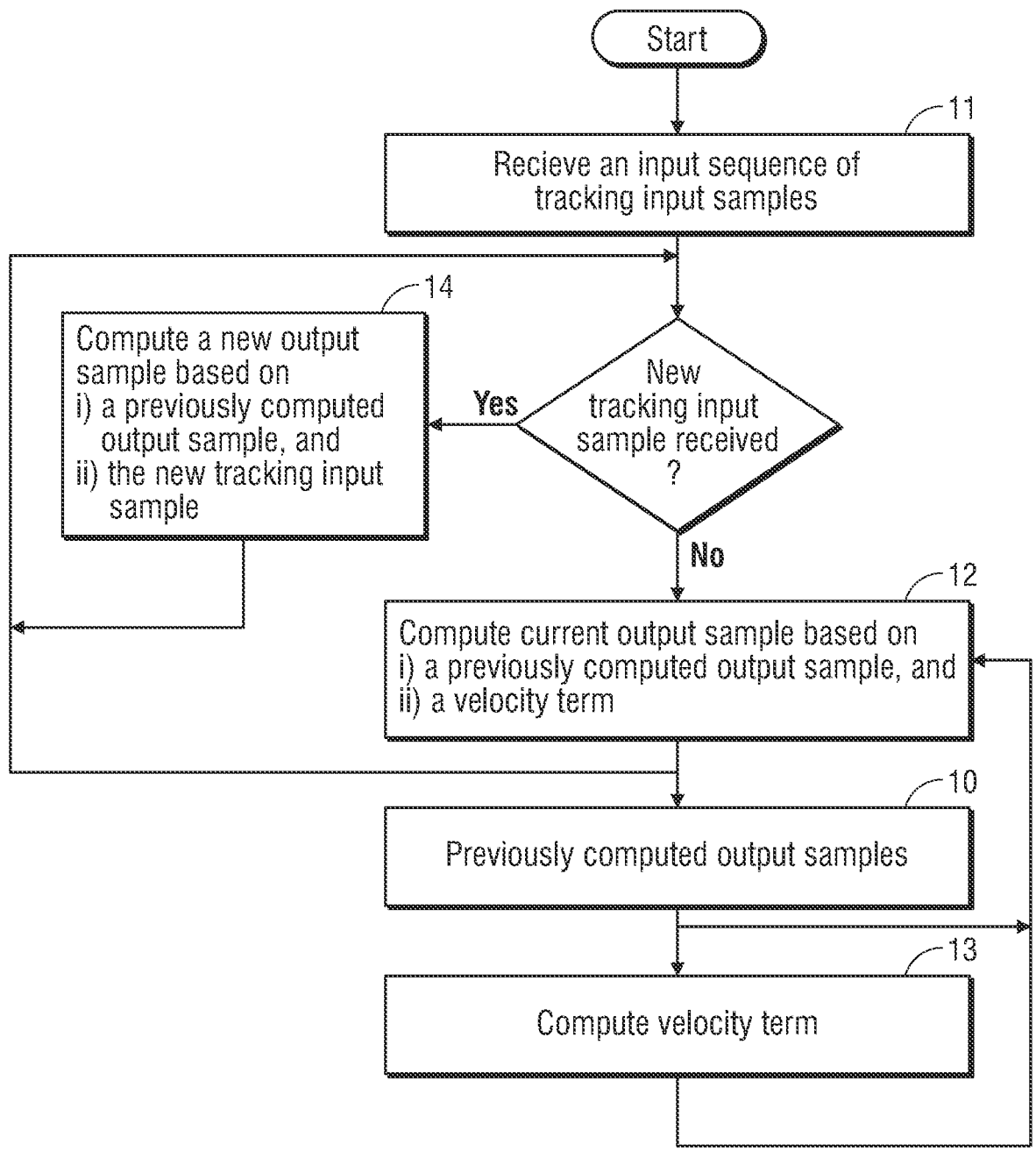
FIG. 6 is a flow diagram of a method performed by a robotic surgery system processor that corrects a UID tracking input.

Referring now to FIG. 6, this is flow diagram of a method performed by a robotic surgery system that has a processor and a machine-readable medium having stored therein instructions that when executed by the processor correct a UID tracking input, by producing an output sequence that is an estimate of a position or an orientation of the UID. In operation 11, the processor receives an input sequence that are measures of the position or the orientation of the UID, and computes a current output sample of the output sequence (operation 12), wherein the current output sample is computed based on i) a previously computed output sample (operation 10), and ii) a computed velocity term (operation 13). When a new tracking input sample of the input sequence (operation 11) is received, a new output sample of the output sequence is computed (operation 14), based on i) a previously computed output sample (operation 10), and ii) the new tracking input sample.

ADDITIONAL THOUGHTS

While elements of position such as (x, y, z) coordinates are orthogonal or independent from each other in the sense that each could be filtered independently of the others and using a non-estimating, low pass filter, orientation elements such as (pitch, yaw, roll) or quaternion (3 angles, and 1 length) are not all independent from each other and as such need an estimating-type filter like the LQE 6 described above for the orientation case.

As explained above, an embodiment of the invention may be an article of manufacture in which a machine-readable medium (such as microelectronic memory) has stored therein instructions which program one or more data processing components (generically referred to here as "a processor" that executes the instructions) to perform the digital signal processing operations of the LQE 6 described above for correcting the UID tracking input. In other embodiments, some of these operations might be performed by specific hardware components that contain hardwired logic (e.g., dedicated digital filter blocks and state machines). Those operations might alternatively be performed by any combination of programmed data processing components and fixed hardwired circuit components.

While certain embodiments have been described and shown in the accompanying drawings, it is to be understood that such embodiments are merely illustrative of and not restrictive on the broad invention, and that the invention is not limited to the specific constructions and arrangements shown and described, since various other modifications may occur to those of ordinary skill in the art. For example, while a robotic surgery UID is held in a hand of a user, the tracking input correction techniques described above are also applicable to other applications including where the UID is attached to a head or to another limb of a user such as a leg or foot. The description is thus to be regarded as illustrative instead of limiting.

What is claimed is:

1. A method comprising:
receiving an input sequence of input samples that track position or orientation of an input device of a robotic surgery system,
while a new input sample in the input sequence has not been received, computing a current output sample, wherein the current output sample is computed based on i) a previously computed output sample, and ii) a velocity term, and
when the new input sample is received, computing a new output sample, based on i) a previously computed output sample, and ii) the new input sample; and
producing an output sequence that includes the current output sample and the new output sample.

2. The method of claim 1 wherein computing the current output sample is based on a tuning parameter that adjusts a sample-to-sample time interval used in a system model of the input device.

3. The method of claim 2 wherein the sample-to-sample time interval comprises a sum of i) the tuning parameter and ii) a nominal sampling period of the output sequence.

4. The method of claim 2 wherein the input sequence has a sampling rate that is lower than that of the output sequence.

5. The method of claim 1 wherein when the new input sample is received, the new output sample is computed by computing a Kalman filter gain.

6. The method of claim 1 wherein the input sequence comprises a sequence of orientation vectors, and the output sequence comprises an estimate of orientation of the input device.

7. The method of claim 1 wherein while the new input sample has not been received, the current output sample is computed from a window of a plurality of previously computed output samples, by a) fitting a line to the previously computed output samples in the window, and b) taking a derivative of the line to be the velocity term.

8. The method of claim 7 further comprising
wherein while the new input sample has not been received, computing a next output sample based on i) another previously computed output sample, and ii) another velocity term, by
moving the window forward so that another plurality of previously computed output samples are within the window, and
repeating a) and b) using said another plurality of previously computed output samples to compute said another velocity term.

9. The method of claim 7 wherein when the new input sample is received the new output sample is computed using the previously computed output sample, the new input sample, and not a velocity term.

10. The method of claim 1 wherein when the new input sample is received the new output sample is computed using the previously computed output sample, the new input sample, and not a velocity term.

11. An article of manufacture comprising:
a machine-readable medium having stored therein instructions that when executed by a processor of a robotic surgery system
receive an input sequence of input samples that are measures of position or orientation of an input device,
while a new input sample in the input sequence has not been received, compute a current output sample, wherein the current output sample is computed based on a tuning parameter that adjusts a sample-to-sample time interval used in a system model of the input device,
when the new input sample is received, compute a new output sample, based on i) a previously computed output sample, and ii) the new input sample, and
producing an output sequence that includes the current output sample and the new output sample.

12. The article of manufacture of claim 11 wherein the sample-to-sample time interval, used in the system model of the input device, comprises a sum of i) the tuning parameter and ii) a nominal sampling period of the output sequence.

13. The article of manufacture of claim 12 wherein when the new input sample is received, the new output sample is computed by computing a Kalman filter gain.

14. The article of manufacture of claim 13 wherein the input sequence has a sampling rate that is lower than that of the output sequence.

15. The article of manufacture of claim 11 wherein the input sequence comprises a sequence of orientation vectors, and the output sequence comprises an estimate of the orientation of the input device.

16. The article of manufacture of claim 11 wherein when the new input sample is received, the new output sample is computed by computing a Kalman filter gain.

17. The article of manufacture of claim 16 wherein the input sequence has a sampling rate that is lower than that of the output sequence.

18. The article of manufacture of claim 11 wherein the medium has stored therein instructions that when executed by the processor,
while the new input sample in the input sequence has not been received, compute the current output sample based on i) a previously computed output sample, and ii) a velocity term.

19. The article of manufacture of claim 18 wherein
the current output sample is computed from a window of a plurality of previously computed output samples, by
a) fitting a line to the previously computed output samples in the window, and b) taking a slope of the line to be the velocity term.

20. The article of manufacture of claim 11 wherein the input sequence has a sampling rate that is lower than that of the output sequence.

* * * * *